United States Patent
Rao et al.

(10) Patent No.: US 9,296,705 B2
(45) Date of Patent: Mar. 29, 2016

(54) 4-TERT-BUTYL-N-[6-(2-HYDROXYETHOXY)-5-(2-METHOXYPHENOXY)-2(2-PYRIMIDINYL)-PYRIMIDINE-4-YL)-BENZENESULFONAMIDE SODIUM

(71) Applicant: Davuluri Ramamohan Rao, Hyderabad (IN)

(72) Inventors: Davuluri Ramamohan Rao, Hyderabad (IN); Ponnaiah Ravi, Madurai (IN); Bathini Guruswamy, Hyderabad (IN); Praveen Kumar Neela, Hyderabad (IN); Narayana Venugopala Rao, Medak (IN); Somepalli Prasad, Hyderabad (IN); Dongari Naresh, Nalagonda (IN)

(73) Assignee: Davuluri Ramamohan Rao, Hyderabad (IN)

( * ) Notice: Subject to any disclaimer, the term of this patent is extended or adjusted under 35 U.S.C. 154(b) by 0 days.

(21) Appl. No.: 14/425,108

(22) PCT Filed: Aug. 29, 2013

(86) PCT No.: PCT/IN2013/000529
§ 371 (c)(1),
(2) Date: Mar. 2, 2015

(87) PCT Pub. No.: WO2014/033758
PCT Pub. Date: Mar. 6, 2014

(65) Prior Publication Data
US 2015/0232430 A1    Aug. 20, 2015

(30) Foreign Application Priority Data
Aug. 31, 2012   (IN) .............. 3618/CHE/2012

(51) Int. Cl.
*A61K 31/506*   (2006.01)
*C07D 239/69*   (2006.01)
*C07D 403/04*   (2006.01)

(52) U.S. Cl.
CPC ........... *C07D 239/69* (2013.01); *C07B 2200/13* (2013.01)

(58) Field of Classification Search
CPC ............. C07B 2200/13; C07D 239/69; C07D 403/04; A61K 31/506
See application file for complete search history.

(56) References Cited

U.S. PATENT DOCUMENTS

2011/0014291 A1 *   1/2011   Dixit ................... C07D 403/04
                                                           424/489

FOREIGN PATENT DOCUMENTS

WO   WO2009083739 A1   7/2009
WO   WO2011058524 A2   5/2011

* cited by examiner

*Primary Examiner* — Erich A Leeser
(74) *Attorney, Agent, or Firm* — Ling Wu; Stephen Yang; Ling and Yang Intellectual Property

(57) ABSTRACT

A process for the purification of Bosentan sodium and a novel crystalline form of substantially pure Bosentan sodium to disclosed in this invention.

4 Claims, 4 Drawing Sheets

4-TERT-BUTYL-N-[6-(2-HYDROXYETHOXY)-5-(2-METHOXYPHENOXY)-2(2-PYRIMIDINYL)-PYRIMIDINE-4-YL)-BENZENESULFONAMIDE SODIUM

CROSS REFERENCE TO RELATED APPLICATION

This application claims priority from the provisional specification No. 3618/CHE/2012 filed on Aug. 31, 2012.

FIELD OF THE INVENTION

The present invention provides a purification method of 4-tert-butyl-n-[6-(2-hydroxyethoxy)-5-(2-methoxyphenoxy)-2-(2-pyrimidinyl)-pyrimidine-4-yl] benzenesulfonamide sodium and a novel polymorphic form of the Bosentan sodium.

BACKGROUND OF THE INVENTION

4-Tert-butyl-n-[6-(2-hydroxyethoxy)-5-(2-methoxyphenoxy)-2-(2-pyrimidinyl)-pyrimidine-4-yl]-benzenesulfonamide, monohydrate also known as Bosentan monohydrate is represented by structural formula (I).

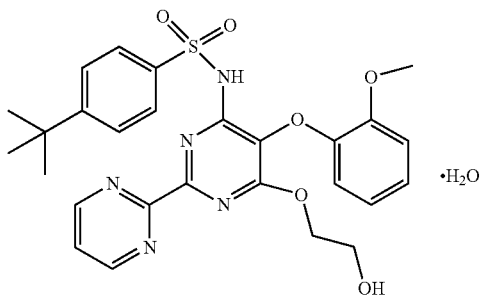

Bosentan is first disclosed in, the U.S. Pat. No. 5,292,740 and used in the treatment of pulmonary arterial hypertension (PAH) to improve exercise capacity and symptoms in patients with grade III functional status.

The U.S. Pat. No. 5,292,740 (hereinafter referred as US'740) discloses a method for the preparation of Bosentan sodium (formula III) involving the reaction of chloropyrimidin benzenesulfonamide (formula II) with sodium metal in ethylene glycol. Bosentan sodium (formula III) is employed for the preparation of Bosentan Formula I)

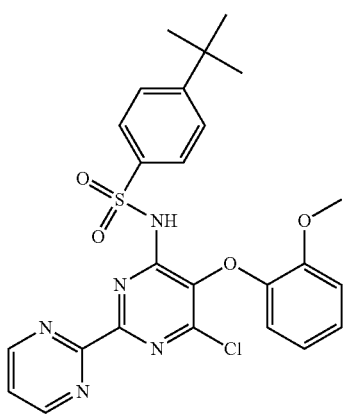

chloro bipyrimidine benzene sulfonamide

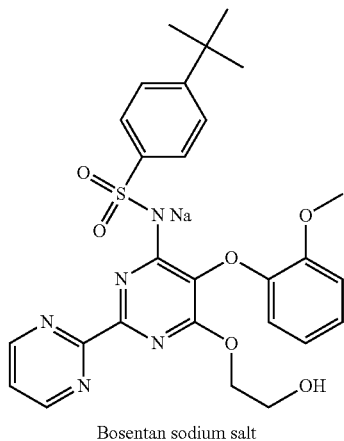

Bosentan sodium salt

The process according to the patent US'740 leads to the formation of undesired ethylene glycol bisulfonamide along with Bosentan which show negative impact on yield of Bosentan. This ethylene glycol bisulfonamide is also known as dimer impurity. Hence Bosentan. prepared according to the patent US'740 requires repeated purification to get desired purity.

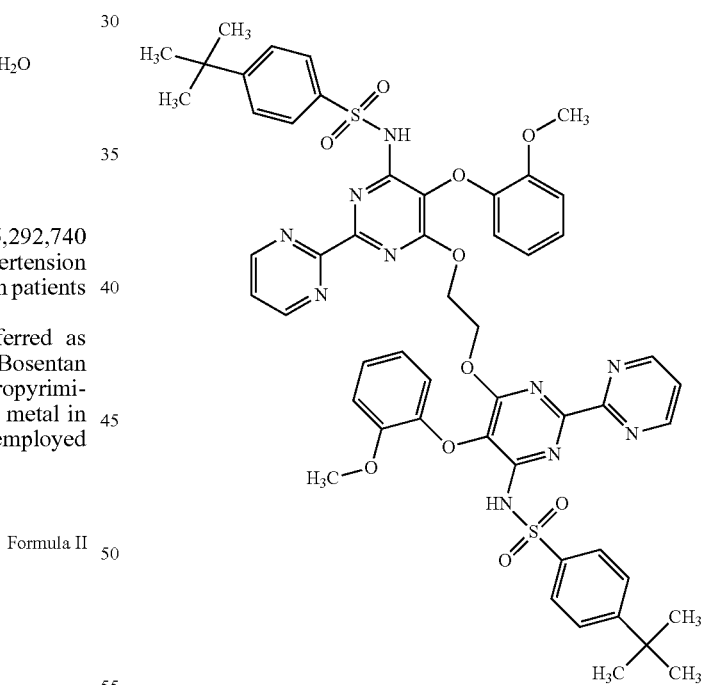

The patent US'740 discloses crystalline Bosentan sodium salt having characteristic peaks of XPRD shown in FIG. 1 and melting point of 195 to 198° C.

The PCT publication WO 2011/058524 discloses form C and form D of Bosentan sodium salt characterized by XPRD values and the process for preparing the same thereof. The PCT publication WO2012056468 discloses the crystalline Bosentan Lithium salt and the process for preparing the same thereof.

SUMMARY OF THE INVENTION

The primary aspect of the present invention is to provide a novel crystalline form of substantially pure Bosentan sodium.

A further aspect of the present invention provides the process for the preparation of the novel crystalline form B of Bosentan sodium salt, characterized by an X-ray powder diffraction pattern having peaks expressed as 2-theta which include 5.5, 7.5, 11.1, 18.9, 22.7±2-theta.

Another aspect of the invention provides a process for the purification of Bosentan sodium comprising the steps of:
 a) adding an organic solvent to Bosentan sodium;
 b) optionally refluxing the mixture obtained in step (a);
 c) adding water to the mixture obtained in step (a) or (b);
 d) treating the mixture obtained in step (c) with activated charcoal;
 e) filtering the reaction mass, optionally washing the filter bed;
 f) optionally heating the filtrate;
 g) cooling the reaction mass; and
 h) filtering the Bosentan sodium.

Yet another aspect of the invention provides bosentan sodium having less than about 0.5% of dimer impurity, preferably 0.2% of dimer impurity.

DESCRIPTION OF THE INVENTION

The present invention provides a process for preparing the highly pure Bosentan sodium having less than about 0.2% of dimer impurity.

The process for preparing the highly pure Bosentan sodium with less than about 0.2% of dimer impurity comprising the steps of:
 a) adding an organic solvent to Bosentan sodium;
 b) optionally refluxing the mixture obtained in step (a);
 c) adding water to the mixture obtained in step (a) or (b);
 d) treating the mixture obtained in step (c) with activated charcoal;
 e) filtering the reaction mass, optionally washing the filter bed;
 f) optionally heating the filtrate;
 g) cooling the reaction mass; and
 h) filtering the Bosentan sodium.

The bosentan sodium used as starting material may be prepared according to the any known prior art methods.

The organic solvent used in the step (a) is selected from the group comprising of polar solvents such as dimethylformamide, acetonitrile and acetone; ethers such as tetrahydrofuran and dioxane; alcohols such as methanol, tert-butanol and i-amylalcohol; fluorinated alcohols such as trifluoroethanol or the mixtures thereof, preferably acetonitrile.

The present invention provides a crystalline Form B of Bosentan sodium.

Figure 1:
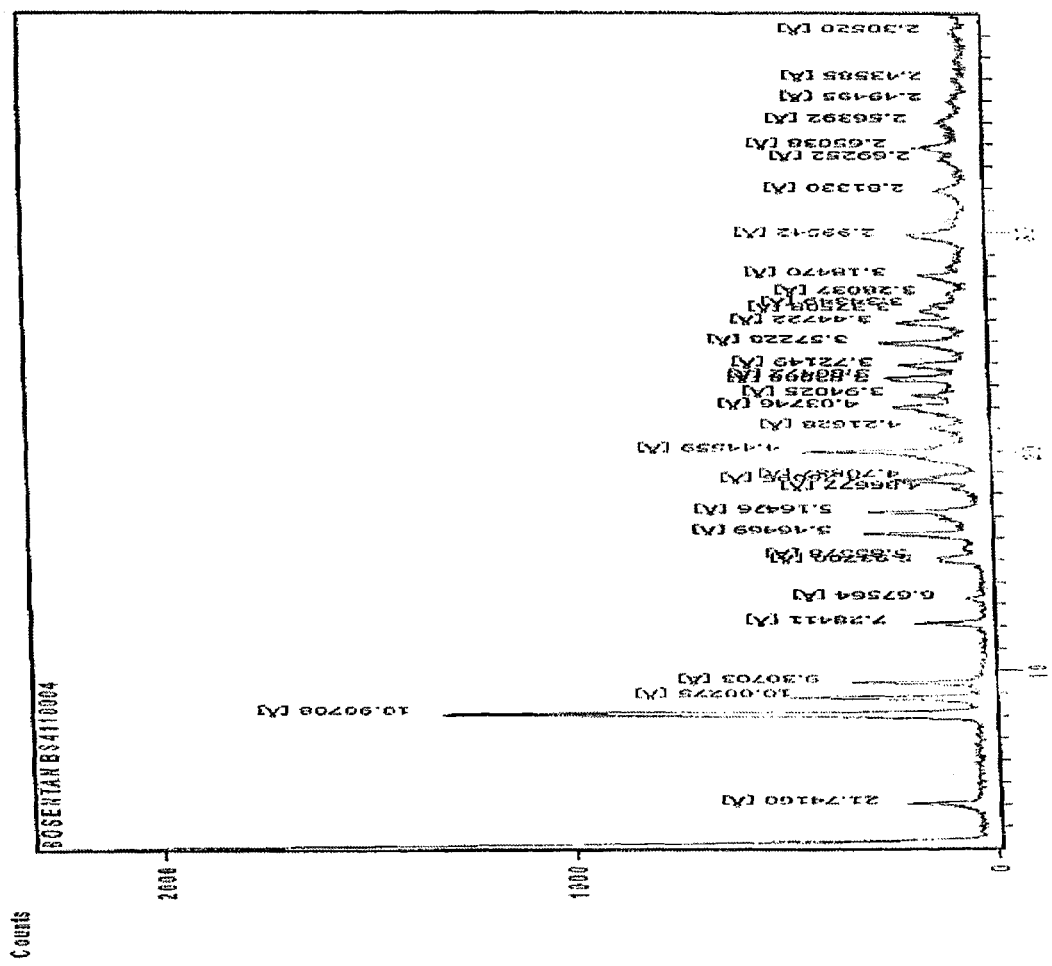
FIG. 1 depicts X-Ray Powder Diffraction (XRPD) pattern of Form A of Bosentan sodium.
Figure 2:
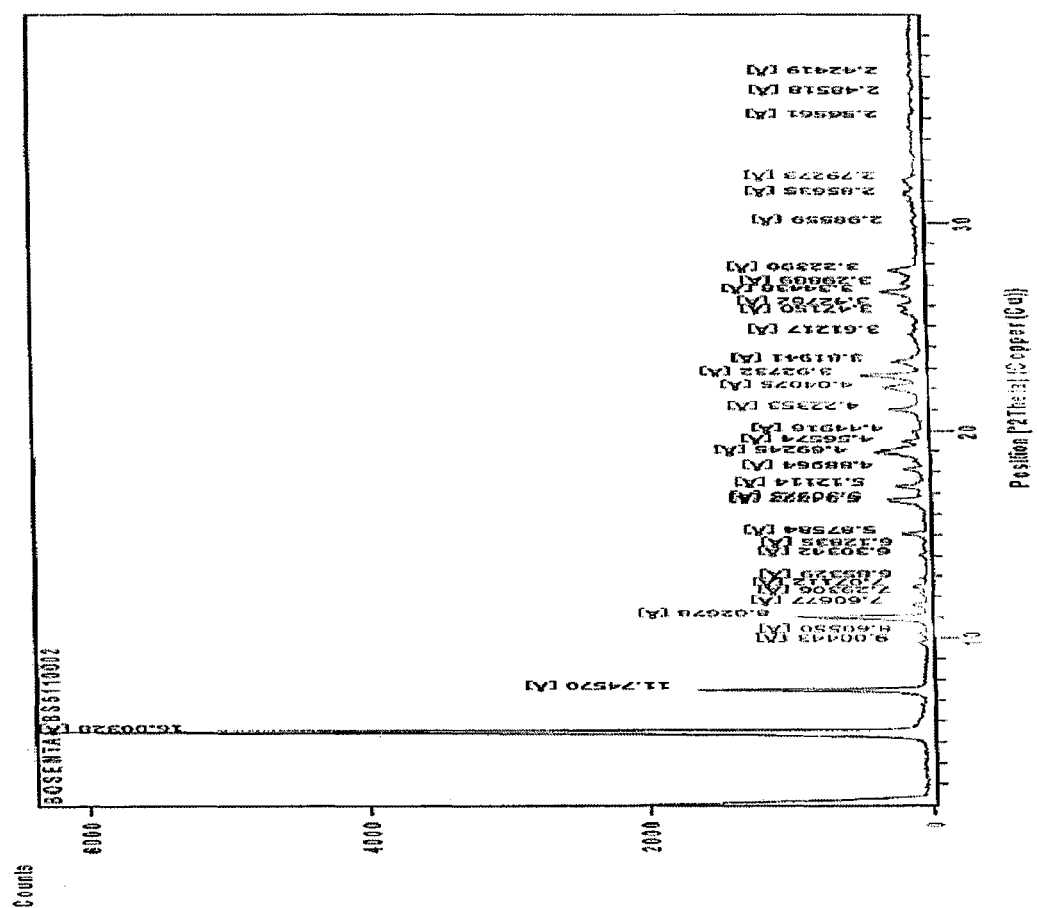
FIG. 2 depicts X-Ray Powder Diffraction (XRPD) pattern of Form B of Bosentan sodium.

The crystalline form B of Bosentan sodium has substantially the same XRPD pattern as depicted in FIG. 2.

The XRPD of crystalline Form B of Bosentan sodium characterized by an X-ray powder diffraction pattern having peaks expressed in 2-theta which includes 5.5, 7.5, 11.1, 18.9, 22.7±2-theta and further peaks at 9.77, 10.24, 11.60, 12.21, 12.56, 12.89, 14.06, 14.59, 15.11, 16.71, 17.40, 18.11, 19.20, 19.60, 19.96, 21.12, 21.99, 22.24, 23.41, 24.59, 25.80, 26.10, 26.86, 27.96, 30.16, 31.48, 32.26, 35.18, 37.37±2-theta.

Figure 3:
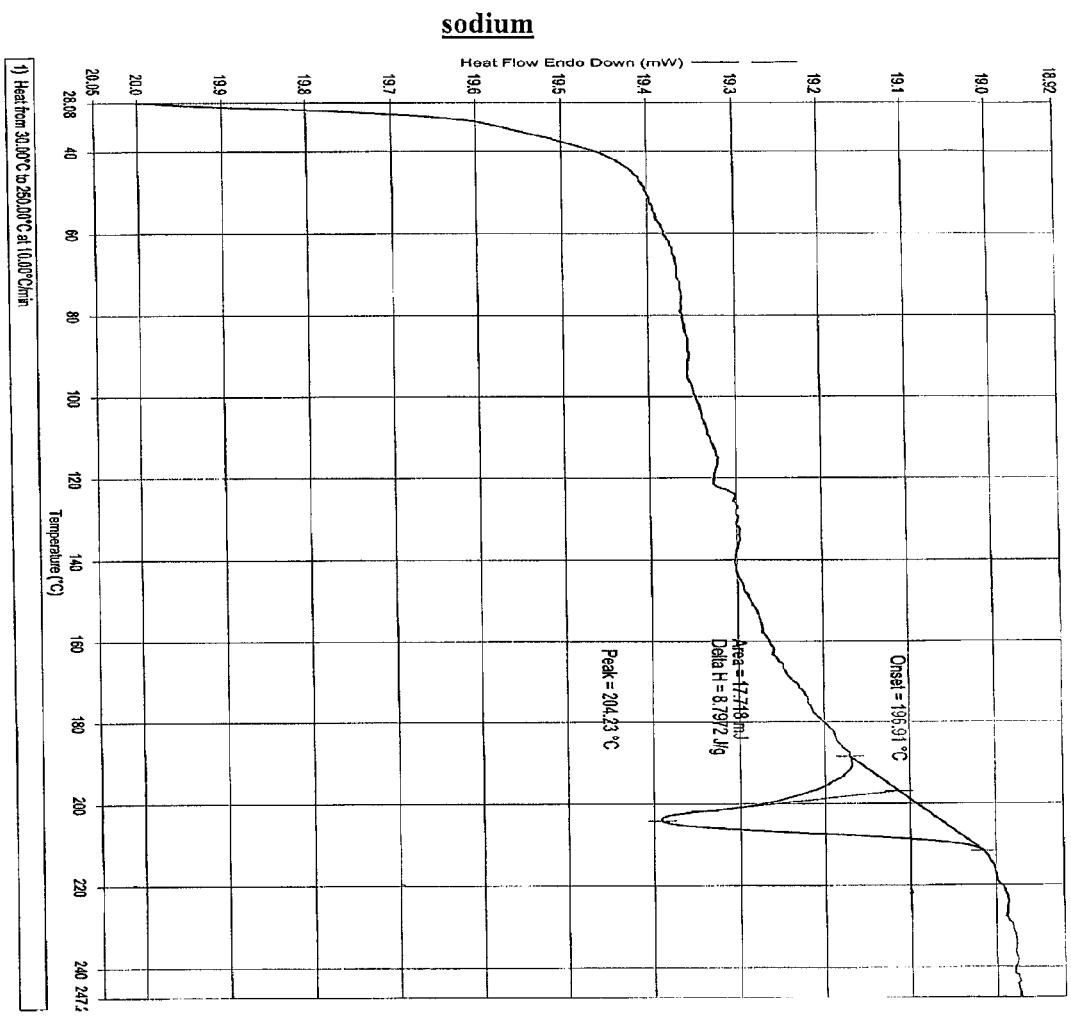
FIG. 3 depicts Differential Scanning calorimetry (DSC) pattern of Form B of Bosentan sodium.

The DSC has substantially the same pattern as depicted in FIG. 3. The DSC exhibits one melting endotherm between about 204±3° C.

Figure 4:
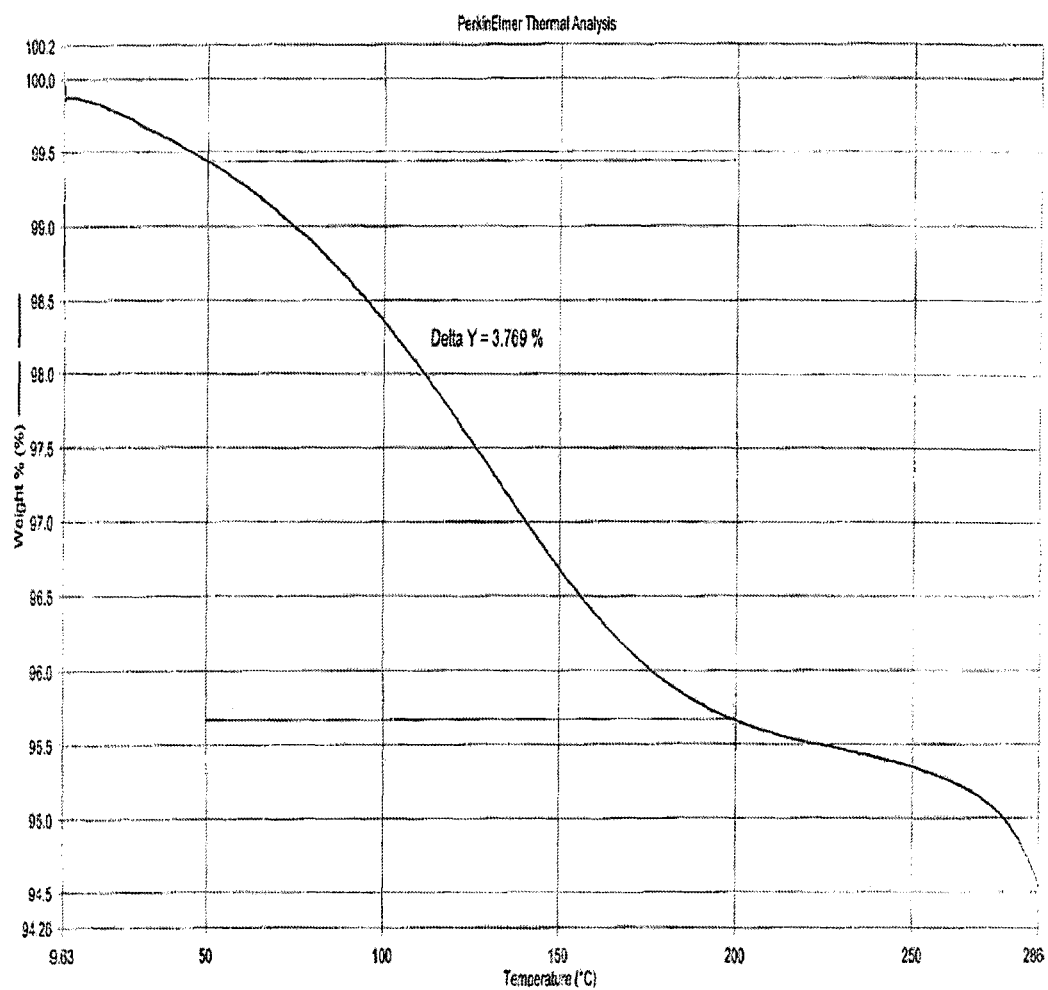
FIG. 4 depicts Thermal Gravimetric Analysis (TGA) of Form B of Bosentan sodium.

A weight loss of about 3.0% to about 3.7% at a temperature of about 50° C. to about 200° C. is observed as measured by TGA (FIG. 4).

The present invention provides a process for preparing novel crystalline Form B of Bosentan sodium salt, characterized by an X-ray powder diffraction pattern having peaks expressed as 2-theta which includes 5.5, 7.5, 11.1, 18.9, 22.7±2-theta comprising the steps of:
 a) adding an organic solvent to Bosentan sodium;
 b) optionally refluxing the mixture obtained in step (a);
 c) adding water to the mixture obtained in step (a) or (b);
 d) treating the mixture obtained in step (c) with activated charcoal;
 e) filtering the reaction mass, optionally washing the filter bed;
 f) optionally heating the filtrate;
 g) cooling the reaction mass; and
 h) filtering the Bosentan sodium.

The organic solvent used in the step (a) is selected from the group comprising of polar solvents such as dimethylformamide, acetonitrile and acetone; ethers such as tetrahydrofuran and dioxane; alcohols such as methanol, tert-butanol and i-amylalcohol; fluorinated alcohols such as trifluoroethanol or the mixtures thereof, preferably acetonitrile.

Crystalline Bosentan Sodium prepared in the present process has less than about 0.2% of dimer impurity.

Crystalline Bosentan Sodium prepared in the present process may be employed in the preparation of Bosentan monohydrate.

The following example provided in the disclosure is given for the purpose of illustrating the present invention and are not intended to limit the scope on the scope of the invention in any manner.

EXAMPLES

Example 1

Method for Preparing Bosentan Sodium

Sodium hydroxide (19 g) was suspended in Ethylene glycol (300 ml) and heated to 55° C., and maintained for 30 min at the same temperature. Chloro-pyrimidine benzenesulfonamide (100 g) was added into the reaction mixture at 55° C. and slowly the temperature was raised up to 93° C. The reaction mixture was maintained at 93° C. for 5 hours. After cooling the reaction mixture to 55° C., water (1000 ml) was slowly added into the reaction mixture. The reaction was then cooled to room temperature and maintained for one hour at the same temperature. The resultant solid was filtered, washed with water (100 ml) and dried.

Yield=95%; Dimmer impurity: more than 2.5%.

Method for Preparing Bosentan Sodium Form B:

A mixture of Bosentan sodium (100 gm) and acetonitrile (450 ml) was heated up to reflux temperature for 15 min, and then purified water was added drop wise up to hazy solution at the reflux temperature. The reaction mixture was stirred for 15 min and added activated charcoal. The reaction mixture was stirred for 30 min, filtered and washed with acetonitrile. The filtrate was slowly cooled to 25-30° C. for 3 hours and maintained for 1 hour at the same temperature. The resultant solid was filtered and dried at vacuum.

The wet material (168 gm) was suspended in acetonitrile (360 ml) at 30° C., heated to 85° C. and maintained for 15 minutes at the same temperature. Purified water was slowly added to the contents at 85° C. till formation of clear solution and maintained for 30 minutes at the same temperature. The contents were cooled to 30° C. for 3 hours and maintained at the same temperature for 1 hour. The resultant solid was filtered, washed with acetonitrile (100 ml) and dried at 65° C. for 10 hours.

Yield=65.7%; HPLC purity: 99.7%; Dimmer impurity: less than 0.2%.

We claim:

1. A novel crystalline form B of bosentan sodium salt, characterized by an x-ray powder diffraction pattern having peaks expressed in 2-theta which includes 5.5, 7.5, 11.1, 18.9, 22.7±2-theta.

2. A process for preparing crystalline form B of bosentan sodium salt as claimed in claim 1, comprising the steps of:
   a) adding an organic solvent to bosentan sodium;
   b) optionally refluxing the mixture obtained in step (a);
   c) adding water to the mixture obtained in step (a) or (b);
   d) treating the mixture obtained in step (c) with activated charcoal;
   e) filtering the reaction mass, optionally washing the filter bed;
   f) optionally heating the filtrate;
   g) cooling the reaction mass; and
   h) filtering the bosentan sodium.

3. The process according to the claim 2, wherein said organic solvent is acetonitrile.

4. The process according to the claim 2, wherein said crystalline form B of bosentan sodium salt has less than 0.2% of dimer impurity.

* * * * *